US009916958B1

(12) United States Patent
Bhandari et al.

(10) Patent No.: US 9,916,958 B1
(45) Date of Patent: Mar. 13, 2018

(54) ALKALI SEMI-METAL FILMS AND METHOD AND APPARATUS FOR FABRICATING THEM

(71) Applicants: Harish B. Bhandari, Brookline, MA (US); Vivek V. Nagarkar, Weston, MA (US); Olena E. Ovechkina, Alston, MA (US); Henry J. Frisch, Chicago, IL (US); Klaus Attenkofer, Riverhead, NY (US); John M. Smedley, Shirley, NY (US)

(72) Inventors: Harish B. Bhandari, Brookline, MA (US); Vivek V. Nagarkar, Weston, MA (US); Olena E. Ovechkina, Alston, MA (US); Henry J. Frisch, Chicago, IL (US); Klaus Attenkofer, Riverhead, NY (US); John M. Smedley, Shirley, NY (US)

(73) Assignees: RADIATION MONITORING DEVICES, INC., Watertown, MA (US); THE UNIVERSITY OF CHICAGO, Chicago, IL (US); BROOKHAVEN SCIENCE ASSOCIATES, LLC, Upton, NY (US)

( * ) Notice: Subject to any disclaimer, the term of this patent is extended or adjusted under 35 U.S.C. 154(b) by 259 days.

(21) Appl. No.: 14/608,777

(22) Filed: Jan. 29, 2015

Related U.S. Application Data

(60) Provisional application No. 61/933,526, filed on Jan. 30, 2014, provisional application No. 62/003,888, filed on May 28, 2014.

(51) Int. Cl.
*H01J 9/00* (2006.01)
*H01J 9/12* (2006.01)
(Continued)

(52) U.S. Cl.
CPC ............. *H01J 9/12* (2013.01); *C23C 14/025* (2013.01); *C23C 14/165* (2013.01);
(Continued)

(58) Field of Classification Search
CPC ........................................................ H01J 9/12
See application file for complete search history.

(56) References Cited

U.S. PATENT DOCUMENTS 5,972,506 A * 10/1999 Leichter ................. C06C 15/00
    252/506
2001/0044563 A1* 11/2001 Steinbrenner ............ B01J 23/04
    585/452

(Continued)

FOREIGN PATENT DOCUMENTS

EP          2186917 A1     5/2010

OTHER PUBLICATIONS

Lyashenko et al., "Development of high-gain gaseous photomultipliers for the visible spectral range," 2009, IOP Publishing for SISSA, pp. 1-24.*

(Continued)

*Primary Examiner* — Robert A Vetere
(74) *Attorney, Agent, or Firm* — Burns & Levinson LLP; Orlando Lopez

(57) ABSTRACT

Methods and systems for fabricating a film, such as, for example, a photocathode, having a tailored band structure and thin-film components that can be tailored for specific applications, such as, for example photocathode having a high quantum efficiency, and simple components fabricated by those methods.

35 Claims, 9 Drawing Sheets

(51) Int. Cl.
  *H01J 1/34*   (2006.01)
  *H02S 50/15*   (2014.01)
  *G01N 21/63*   (2006.01)
  *C23C 14/02*   (2006.01)
  *C23C 14/16*   (2006.01)
  *C23C 14/54*   (2006.01)
  *C23C 14/34*   (2006.01)

(52) U.S. Cl.
  CPC ........ *C23C 14/3414* (2013.01); *C23C 14/545* (2013.01); *G01N 21/63* (2013.01); *H01J 1/34* (2013.01); *H02S 50/15* (2014.12)

(56) References Cited

U.S. PATENT DOCUMENTS

2002/0157611 A1* 10/2002 Bondestam ........... C23C 16/301
              118/725
2006/0162662 A1* 7/2006 Sato ..................... C23C 14/543
              118/726
2008/0121137 A1* 5/2008 van Osten ........... C23C 14/3414
              106/1.18

OTHER PUBLICATIONS

Karkare et al., "Advances in Photocathode Technology at Cornell University," 2013, PAC2013, pp. 391-393.*
Ettema et al., "Electronic structure of Cs2KSb and K2CsSb," 2002, Phys. Rev. B 66, p. 115102.*
Bhandari et al. "Hot wall Evaporation of High-Sensitivity, High-Resolution CeBr3 Scintillator." IEEE Trans. Nuclear Sci. 59.5(2012):2196-2200.
Lerner et al. "Theoretical Analysis of a Geis-Spindt Cold Cathode Diamond Emitter." J. Physique. 6(1996):39-42.

* cited by examiner

ALKALI SEMI-METAL FILMS AND METHOD AND APPARATUS FOR FABRICATING THEM

CROSS REFERENCE TO RELATED APPLICATIONS

This application claims priority of U.S. Provisional Application No. 61/933,526, entitled ALKALI ANTIMONIDE FILMS AND METHOD AND APPARATUS FOR FABRICATING THEM, filed on Jan. 30, 2014, and U.S. Provisional Application No. 62/003,888, entitled ALKALI SEMI-METAL FILMS AND METHOD AND APPARATUS FOR FABRICATING THEM, filed on May 28, 2014, all of which are incorporated by reference herein in their entirety and for all purposes.

STATEMENT REGARDING FEDERALLY SPONSORED RESEARCH OR DEVELOPMENT

This invention was made with government support under Grants No. DE-SC0009540, DE-SC0008172, DE-AC02-98CH10886 and DE-SC0012704, awarded by Department of Energy, and Grant No. PHY-1066014, from the National Science Foundation. The federal government has certain rights in the invention.

BACKGROUND

The present teachings relate to the alkali semi-metal films, where the semi-metal is a semi-metal in Group 15 of the periodic table, and specifically to synthesis of alkali semi-metal compounds and methods for fabricating films from a pre-synthesized alkali semimetal material.

In one exemplary instance, the alkali semimetal compound is an alkali antimonide. Alkali antimonide films have a number of applications, one of them being high quantum efficiency photocathodes. High quantum efficiency photocathodes have a variety of applications—from photodetectors to light sources. Photocathode is the first element in vacuum-tube-based photodetectors, such as discrete-dynode photomultipliers or microchannel-based photomultipliers, which converts photons or light particles into electrons. Photocathode of a photodetector dictates the fundamental detector properties including quantum efficiency (QE), wavelength response, dark current behavior, and time response. In a larger economic scenario, photocathode primarily predominates the production aspects of a photodetector system, and therefore largely determines the production costs associated therewith. Specifically, the QE of photocathode is a key parameter, because the required detection area often scales inversely with the QE and becomes the cost determining element in large systems, such as neutrino detectors. Consequently, photocathodes play an important role in the detection scheme and fuels the competition between solid-state and conventional tube-based detectors, especially where the size of the detector is an essential property and solid-state detectors are not economical to use.

The distribution function of the QE measured on a large number of identical conventional devices is rather wide, and yield studies show that QEs of over 40% are achievable. A systematic study of photo multipliers has triggered the development of new photocathode recipes with typical QEs of 35-42% on an average. However, to date, there is no evidence that this is a fundamental limit of QE and more importantly, it is not even clear what the fundamental limit may be.

Following the state-of-the-art model, the QE of a cathode is determined by efficiencies of three independent steps: 1) the absorption probability of the photon; 2) the transport of the photoelectron to the surface; and 3) the emission of the electron from the surface. In other words, to realize high QE, a photocathode has to absorb photons in a very thin layer to avoid long and lossy transport of the resulting photoelectron to the surface. The material properties of the photocathode should be such that they minimize inelastic electron scattering to avoid energy loss of the photoelectron on its way to the surface. Further, the photocathode should have a low surface barrier to allow effective emission even for low energy electrons.[Spicer]

A closer look at the band structure of multi-alkali antimony materials reveal that this group is perfectly suited for the desired photocathode. The strong s-p character of the valence and conduction band results in very flat and non-dispersive bands, so that a very high density of occupied states is available within a small energetic window. Also, a very high density of unoccupied states is at the bottom of the conduction band. This structure has two important ramifications: 1) the absorption cross section of a photon is extremely high for photons with energy exceeding the bandgap energy of the material, requiring a few tenths nanometers thickness of cathode materials for efficient absorption; and 2) due to the narrow valence band, the kinetic energy distribution of the photoelectrons is also very narrow, maximizing the effect of the so-called magic window. This is the effect where conduction band electrons cannot scatter with valence band electrons and lose their energy as long as the kinetic energy is smaller than the band gap, e.g., the photon energy is smaller than twice the band gap. Another important aspect of multi-alkali antimony cathodes is the positive electron affinity of their surface, where the surface barrier is just high enough to suppress thermally excited electrons, but is permeable for the un-scattered photoelectrons.

Improvements to produce higher QE fall into two distinct areas: (i) material quality, and (ii) device design.

Material quality. Cathode materials produced following commercial recipes show a very structured surface like an array of nano-pillars. A detailed analysis of the speciation and materials composition shows that the material has multiple compounds with segregations of compounds. This most likely results in areas of high QE and others with nearly no photo-response at all.

Lack of device design. A conventional photocathode does not introduce an electric field inside the cathode to break the symmetry and to force the transport of randomly moving photoelectrons towards the cathode surface.

Therefore, there is a need to develop a new photocathode by resolving the above and other issues, so as to have higher quantum efficiency and/or having wider applicability and/or having more uniform fabrication than conventional photocathodes, and a fabrication method thereof.

There is also a need for thin-film components with a tailored band structure and for fabrication methods thereof.

There is also a further need for thin-film components that can be tailored to specific applications.

SUMMARY

Methods and systems for fabricating a film, such as, for example, a photocathode, having a tailored band structure and thin-film components that can be tailored for specific applications, such as, for example photocathode having a high quantum efficiency, and simple components fabricated by those methods are disclosed herein below.

In one or more embodiments, the method of these teachings for synthesizing an alkali semi-metal compound, where the semimetal is a semi-metal in Group 15 of the periodic table, includes mixing a first alkali material and a second alkali material to form a liquid alloy composition and mixing a solid semi metal material and the liquid alloy composition to form a ternary crystal compound.

In one or more embodiments, the method of these teachings for fabricating a film, such as, for example, a photocathode, includes providing a pre-synthesized alkali semi metal material, where the alkali semimetal material has one or more alkali materials and a semi metal from Group 15 of the periodic table, and depositing a thin film of the pre-synthesized alkali semi metal material on a substrate to form a thin-film component.

In one or more embodiments, the method of these teachings for fabricating a film includes depositing antimony on a substrate and wetting the antimony film on the substrate with liquid pre-synthesized antimonide material.

In one or more embodiments, the apparatus of these teachings for fabricating a thin film component includes a deposition subsystem configured to deposit an alkali semi metal film on a substrate, the film being obtained from depositing a pre-synthesized semimetal material, where the semi metal is a semi-metal from Group 15 of the periodic table, on the substrate.

In one or more instances, the apparatus of these teachings for fabricating a photocathode film also includes a characterization member configured to measure a quantum efficiency of the photocathode in real time of the photocathode deposition.

A number of other embodiments of the methods and apparatus of these teachings as well as thin film components fabricated by the methods of these teachings are also disclosed.

For a better understanding of the present teachings, together with other and further objects thereof, reference is made to the accompanying drawings and detailed description and its scope will be pointed out in the appended claims.

DETAILED DESCRIPTION

Figure 1A:
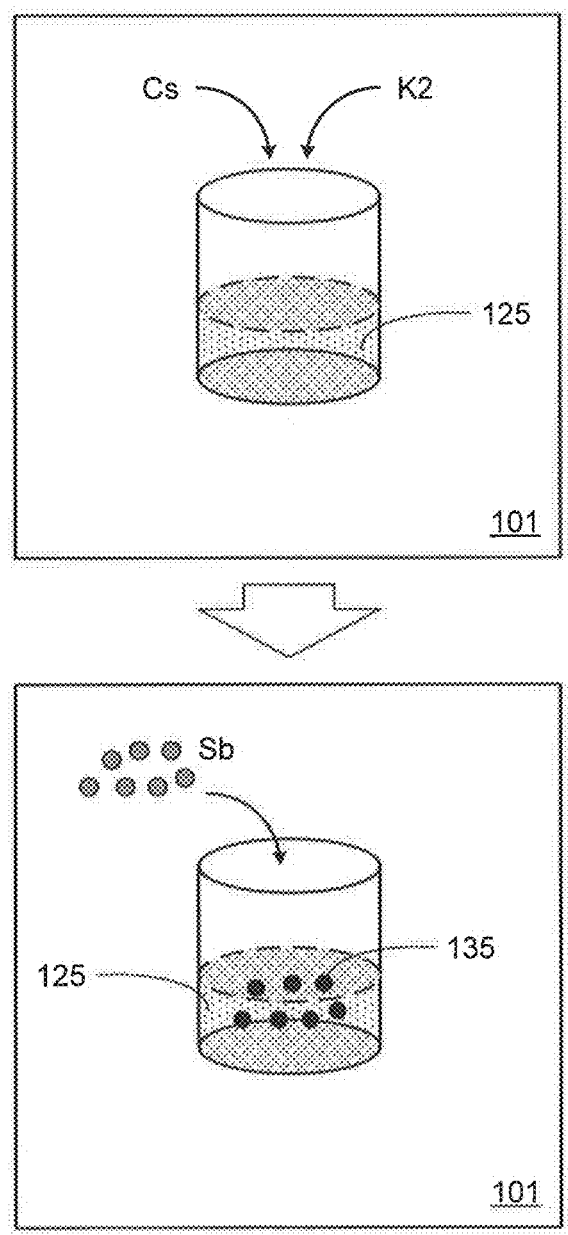
FIG. 1A schematically illustrates the direct synthesis of polycrystalline $K_2CsSb$, in accordance with one embodiment of the present invention.

The present teachings provide a film, such as, for example, a photocathode, having a tailored band structure and thin-film components that can be tailored for specific applications and a fabrication method thereof.

The following detailed description is of the best currently contemplated modes of carrying out these teachings. The description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

"Antimonide," as used herein, refers to compounds of antimony.

"Alkali," as used herein, is a chemical material from Group 1 of the periodic table.

The semi-metals from Group 15 of the periodic table (also referred to as Group Va or the nitrogen group or the pnictogens) include arsenic, antimony and bismuth.

Except where otherwise indicated, all numbers expressing quantities of ingredients, reaction conditions, and so forth used in the specification and claims are to be understood as being modified in all instances by the term "about."

In one or more embodiments, the method of these teachings for synthesizing an alkali semi-metal compound, where the semimetal is a semi-metal in Group 15 of the periodic table, includes mixing a first alkali material and a second alkali material to form a liquid alloy composition and mixing a solid semi metal material and the liquid alloy composition to form a ternary crystal compound.

In an exemplary embodiment, the semi metal is antimony.

In one or more exemplary embodiments, the method of these teachings for synthesizing an alkali antimonide compound includes mixing a first alkali material and a second alkali material to form a liquid alloy composition and mixing a solid antimony material and the liquid alloy composition to form a ternary crystal compound.

In one or more embodiments, the method of these teachings for fabricating a film, such as, for example, a photocathode, includes providing a pre-synthesized alkali semi metal material, where the alkali semimetal material has one or more alkali materials and a semi metal from Group 15 of the periodic table, and depositing a thin film of the pre-synthesized alkali semi metal material on a substrate to form a thin-film component.

In one or more exemplary embodiments, the method of these teachings for fabricating a thin film component includes providing pre-synthesized antimonide material, the antimonide material comprising a first alkali material, a second alkali material and antimony and A) depositing a thin film of an antimonide material on a substrate to form a cathode. In one instance, the first alkali material comprises potassium (K), the second alkali material comprises cesium (Cs) and the antimonide material comprises $K_2CsSb$.

In one or more instances, the method of these teachings for fabricating a photocathode also includes B) measuring a quantum efficiency of the cathode and C) repeating A) and B) until the quantum efficiency is greater than a predetermined value.

In one or more embodiments, the apparatus of these teachings for fabricating a thin film component includes a deposition subsystem configured to deposit an alkali antimonide film on a substrate, the film being obtained from depositing a pre-synthesized antimonide material on the substrate.

In one or more instances, the apparatus of these teachings for fabricating a photocathode film also includes a characterization member configured to measure a quantum efficiency of the photocathode in real time of the photocathode deposition.

To ensure uniformity of stoichiometry and high QE across a large area, methods of photocathode deposition can be used, such as, but not limited to sputtering methods, hot wall evaporation (HWE), e-beam deposition methods, and other forms of evaporation and deposition. In either case, in an exemplary embodiment, the deposited material can be pre-synthesized, stoichiometrically-balanced antimonide material, the antimonide material comprising a first alkali material, a second alkali material and antimony, such as, for example but not limited to, $K_2CsSb$, or various components of the $K_2CsSb$ compound that are independently co-evaporated and allowed to interact on the substrate under appropriate annealing conditions.

Cesium—(Cs) and potassium—(K) antimonides are an interesting class of materials with different stoichiometries (e.g., $K_3Sb$, $Cs_3Sb$, $Cs_2KSb$, and $K_2CsSb$) and with a semiconducting behavior. These antimonides exhibit good optical absorption in the visible region of the light spectrum and low work function, which makes them excellent photo-activated electron emitters, also known as photocathodes. Therefore, this class of materials has been the subject of extensive studies and applications.

In a photocathode, the conversion of incident photons into detectable electrons occurs by the excitation of a valence-band electron to a conduction-band state after the absorption of a photon and the subsequent emission of a photoelectron. The efficiency of conversion, also known as the quantum efficiency (QE), for a given photocathode depends on its electronic properties-mainly the density of states and the band gap. The work function of a surface is strongly affected by the condition of the surface as well. The presence of minute amounts of contamination (less than a complete monolayers of atoms or molecules), or the occurrence of surface reactions (oxidation or similar) can change the work function substantially. Changes of the order of 1 eV are common for metals and semiconductors, depending on the surface condition. Fabrication of high efficiency photocathode is therefore difficult and has to be performed in a contamination free environment. From a technological point of view, the electronic properties of the photocathodes can be influenced towards a higher QE by altering the chemical composition and lattice arrangement within the alkali-antimonides.

Monovalent alkalis ($X^{1+}$, $Y^{1+}$, $Z^{1+}$) react with trivalent semimetals, where the semi-metal is a semi metal from Group 15 in the periodic table, ($SM_{G15}^{3-}$), to form alkali semi metal compounds of the type—$X_3\,SM_{G15}$, $X_2Y\,SM_{G15}$ or $XYZ\,SM_{G15}$. The as-prepared alkali semi-metal compounds have defects as a result of missing alkalis in the semi-metal lattices which act as acceptors and give rise to p-type semiconductors. These alkali semi-metal compounds can be converted to n-type by doping with group II elements that are aliovalent to the alkalis. One example is the introduction of divalent $Ba^{2+}$ into K2CsSb, which will act as a donor and result in an n-type semiconductor. Doping can be achieved in the direct melt synthesis by adding group II elements in ppb concentration range to the alkali alloy prior to reacting with the semi-metal, for example Sb. During the reaction of the alkali alloy with Sb, the heat of reaction will enable the placement of the Ba donor atom within the lattice of the alkali antimonide. The formation of p and n-type semiconductors is important for formation of junction devices.

In order to better elucidate these teachings, a number of exemplary embodiments are presented herein below. But it should be noted that these teachings are not limited to only those exemplary embodiments The calculated electronic band structure of the hexagonal binary compounds—Sb and $K_3Sb$ have been reported to have low density of electron states at the bottom of the conduction band leading to reduced band gaps. In contrast, the cubic phases of the mixed bi-alkali antimonides ($K_2CsSb$ and $CsK_2Sb$) have less dispersive band at the bottom of the conduction band, which result in larger band gaps and thus better photocathode efficiencies. The calculated electronic structures of cubic-phase $K_2CsSb$-based photocathode demonstrate the highest quantum efficiencies for ultraviolet light detection with low thermionic noise, indicating low electron affinity and a relatively large bandgap.

The best performing conventional K—Cs—Sb photocathode provides a quantum efficiency of ~45% at around 400 nm. Although the theoretical-highest efficiency is attributed to the cubic-phased $K_2CsSb$ phase, the composition and structure of the commercial photocathode is not readily available. For research purposes, the bi-alkali photocathodes films have been synthesized in labs via "yo-yo" method where Cs and K vapors are introduced sequentially onto a heated Sb-coated glass substrates. The QE is monitored real-time during the synthesis of a K—Cs—Sb compound and this process is optimized to optimize the QE. This method has had limited success in terms of repeatability, uniformity, complexity of the process of making photocathodes.

Direct Synthesis of Polycrystalline Ternary Crystal Compounds

In one or more embodiments, the method of these teachings for synthesizing a photocathode compound includes mixing a first alkali material and a second alkali material to form a liquid alloy composition and mixing a solid antimony material and the liquid alloy composition to form a ternary crystal compound.

In one instance, the alloy composition is a liquid alloy composition. In one embodiment, wherein the one or more alkali materials comprise a first alkali material and a second alkali material; and wherein the alkali antimonide compound is a crystal compound. In one instance, upon mixing the solid antimony material and the liquid alloy composition, the crystal compound spontaneously forms without external physical interference.

In yet another instance, the method is performed in an enclosed environment having a pressure ranging from about $10^{-10}$ torr to about 3 atm and at a predetermined ambient temperature ranging from about −90° C. to about 800° C. Ranges of low temperatures including room temperature are within the scope of these teachings. In one exemplary embodiment, the predetermined ambient temperature is a low temperature ranging from about 15° C. to about 30° C. In one exemplary embodiment, the predetermined pressure is from about 750 torr to about 800 torr. In one embodiment, the enclosed environment is a non-oxidizing environment containing inert gas, and wherein the enclosed environment is purified to contain less than about 0.5 ppm of oxygen ($O_2$) and water ($H_2O$). In one instance, the inert gas is argon or another noble gas.

In one exemplary embodiment, an approach of these teachings has been developed to synthesize $K_2CsSb$ material. The main emphasis for this exemplary approach of these teachings is on synthesis of $K_2CsSb$ compound whose composition and lattice parameters subscribe to the theoretical values that ensure the highest QE measured so far (for example, up to, but not limited to 80%). The approach involves synthesis of $K_2CsSb$ compound by reaction of K, Cs, and Sb raw materials in bulk under an inert environment.

FIG. 1A schematically illustrates the direct synthesis of polycrystalline $K_2CsSb$, in accordance with one embodiment of the present invention. As shown in FIG. 1A, first, K and Cs alkali are mixed together into an alloy composition 125 of $K_2Cs$ at room temperature. Although the atomic radii of K and Cs differ by ~14%, they form a completely miscible liquid at room temperature, whose reported freezing point is −90° C. To this liquid $K_2Cs$, one molar proportion of Sb material 115 is added in powder or bead format to complete the reaction of $K_2CsSb$ compound, at room temperature. The reaction to form the desired $K_2CsSb$ compound is spontaneous at room temperature and occurs with release of some heat. The final product 135 is a black-colored, highly crystalline powder, which can be further ground to a fine homogenous powder using mortar and pestle. The preparation of the reaction chemicals and their handling are carried out in a glove box 101 with Argon or other noble gas atmosphere which is purified to better than 0.5 ppm of $O_2$ and $H_2O$.

The crystal structure and lattice parameter of the as-synthesized $K_2CsSb$ is studied with a Bruker X-ray diffraction system, using a Molybdenum K1/K2 emission line. The $K_2CsSb$ material is sealed in a 0.8 mm diameter capillary whose wall thickness is about 0.01 mm. The diffraction analysis of the filled capillaries shows sharp peaks indicating highly crystalline material despite being synthesized at room temperature. The location, intensity and broadening of the diffraction peaks match with the theoretical data. The measured data shows negligible background and no additional peaks, indicating pure phase formation. The measured data shows a lattice parameter of 8.615 Å compared to the 8.635 Å calculated from theory. This small difference is expected given that the calculated data refers to the $K_2CsSb$ lattice at 0 K as opposed to 298 K, the temperature at which the compound is synthesized and characterized. Furthermore, the peak broadening indicates that the $K_2CsSb$ compound is a nanocrystalline powder whose crystallites are as small as 15 nm.

Accordingly, one embodiment of the present teachings provides a direct synthesis method for the $K_2CsSb$ material, whose chemical composition and lattice parameters match very well with the calculated theoretical model slated to perform with, for example, up to, but not limited to, 80% QE. This material can be synthesized at room temperature and results in a single homogenous phase, whose crystallites measure 15-30 nm. The synthesized compound is can used to obtain a high efficiency photocathodes, if applied in proper formats.

A high QE photocathode is an optimized structure with substantially optimized absorption of incident photon flux, enhanced transport of the resulting photoelectrons to the photocathode surface, and an optimized work function that permits emission of non-thermalized photo electrons while holding thermally excited carriers back. Device engineering and the ability to produce materials with ballistic transport properties on the length scales of the cathode thickness is the key to fulfill these requirements.

A structure can be grown that allows creating an internal electric field, which drives the photoelectron to the surface of the cathode independent of the original photoelectron propagation. The electric field can either be created by using band-bending mechanisms or by using a doping gradient through the vertical direction of the cathode layer similar to a PN-junction in a diode.

In contrast to the relatively challenging grading doping, one can easily achieve band bending by combining compounds with different band gaps. To produce a good transmission cathode, one needs a wide band gap material on the entrance window followed by a small band gap material. The large number of possible compounds makes this approach relatively easy. However, it is important to know that the length scale over which the band can be bent is strongly dependent on the free carrier density of the material. In other words, this approach requires a good intrinsic growth of the cathode. Materials with 0.8 eV to about 1.5 eV band gap are currently available.

Independent to the approach of creating a band bending, good intrinsic material has to be grown. The conventional yoyo-method is currently the best available technique to achieve this. However it is a very slow growth process and the available process control parameters are insufficient, resulting in a wide variation in production yields.

The characteristic of the conventional yoyo-method is that a thin Sb layer is grown and the Sb can react with the Alkali without the need for a major diffusion processes. In addition, the substrate on which the new layer grows provides the seed structure to build a good crystalline structure parallel to the surface normal out. Using co-deposition methods, which are typically based on co-evaporation, sputtering of a stoichiometric target, or other co-deposition techniques, can create similar growth conditions.

In one embodiment, the method of these teachings includes: (i) developing a deposition method with excellent crystalline growth and low concentration of defects, scattering centers, and electron traps which is cost effective and has good production yield; and (ii) producing a structure that creates an internal electrical field either by grading the band gap or by grading the doping profile. The first step can be, in one instance, made possible by the thermodynamic equilibrium of evaporated species achievable in the deposition method, such as, sputtering or hot wall epitaxial deposition, controlled co-evaporation of constituents in case of e-beam evaporation, and other deposition methods. Some defects are present in any deposition method. The second step is inherently possible by various techniques disclosed herein below, such as, but not limited to, using co-evaporation approach with controlled evaporation of dopant species. Both objectives can be effectively met by the hot wall evaporation method, as well as the e-beam co-evaporation at elevated substrate temperatures. Detailed discussions of the hot wall evaporation and e-beam deposition methods can be found in, for example, U.S. Pat. No. 8,405,035, Bhandari, H. B. et al, Hot Wall Evaporation of High-Sensitivity, High-Resolution CeBr Scintillator, IEEE Transactions on Nuclear Science, Vol. 59, No. 5, Page(s): 2196-2200, U.S. Pat. Nos. 6,012,413, 3,347,701, 3,276,902, which are incorporated herein by reference in their entirety for all purposes.

Synthesis of Polycrystalline $K_2CsSb$ Using Bridgman Technique

Considering the high reactivity of the alkali components as well as the unwanted oxidation of the antimony, the ternary K$_2$CsSb crystals can be synthesized in an enclosed quartz tube system under vacuum. There are largely two approaches.

Figure 1B:
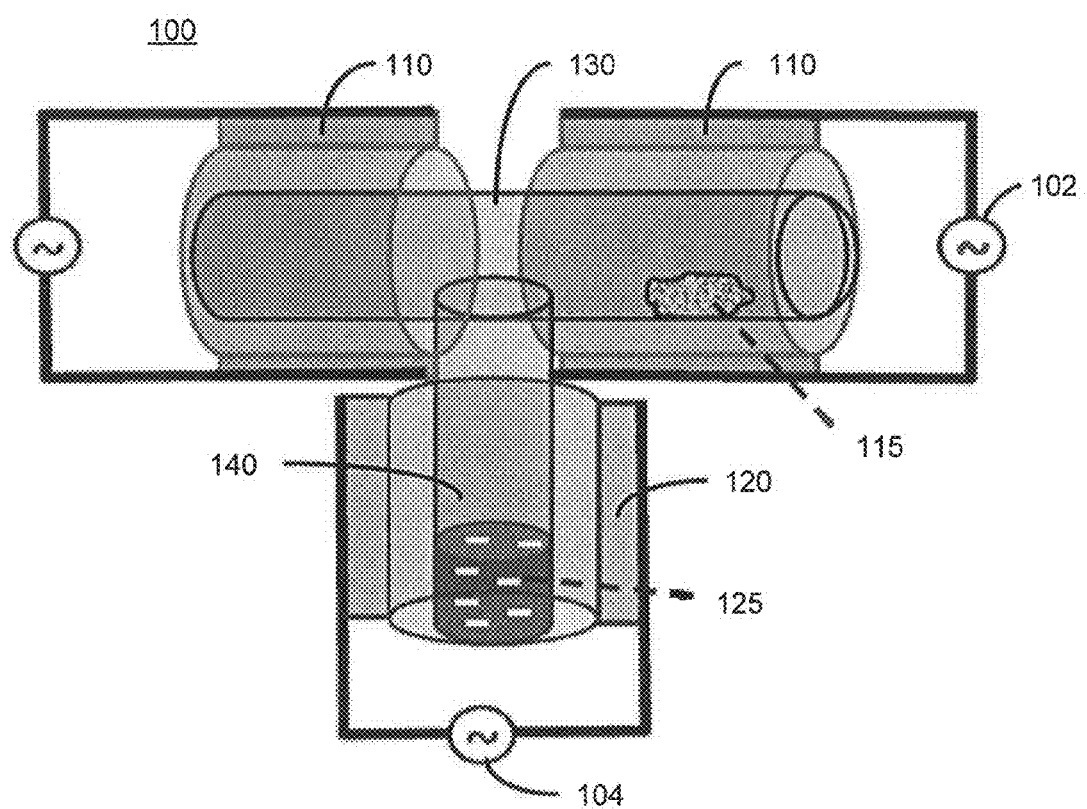
FIG. 1B schematically illustrates a reactor used to synthesize ternary $K_2CsSb$ compound, in accordance with one embodiment of the present teachings.

The first method aims at growing stoichiometric binary intermetallics of Cs$_3$Sb and K$_3$Sb, before preparing the ternary compound. The preparation of the binaries is based on the high diffusivity of the alkali Cs and K into elemental antimony. The method uses two joint quartz tube compartments: a vertical one for the alkali liquids and a horizontal one for the antimony piece FIG. 1B schematically illustrates a reactor for synthesizing ternary K$_2$CsSb compound, in accordance with one embodiment of the present teachings. As shown in FIG. 1B, a reactor 100 includes a first heater 110 wrapping around a horizontal quartz tube 130 and a second heater 120 wrapping around a vertical quartz tube 140. First heater 110 is coupled to a first transformer power supply 102 and heats up horizontal tube 130 at a temperature T1. Second heater 120 is coupled to a second transformer power supply 104 and heats up vertical tube 140 at a temperature T2, where temperature T1 is greater than temperature T2. Vertical tube 140 contains a precursor material 125, such as melted single alkali or K+Cs mixture, for binary precursor preparation. Horizontal tube 130 contains a solid material 115 of, for example, Sb. The quartz tubes 130 and 140 are baked out at 400° C. before each synthesis and sealed after placing the antimony in horizontal tube 140.

The alkalis have high vapor pressure, and thus need hardly any heating (e.g., T2=145° C.), while the alkali diffusion into the antimony needs to be activated at higher temperature in the horizontal portion (e.g., T2=280° C.). The diffusion process is expected to take several hours, thereby providing ordered A3B compounds. Once the binary system is obtained, a high temperature crystal growth technique can be used to form the ternary crystals by mixing the melted Cs$_3$Sb (Tm=725° C.) and the K$_3$Sb (Tm=812° C.) binaries, and cooling the mixture in a well-controlled manner to form homogeneous K$_2$CsSb crystallites.

An alternative methodology is to skip the binary preparation step and use same reactor 100, as shown in FIG. 1B, starting out with antimony and the mixture of cesium and potassium. By optimizing T1 and T2, while utilizing the same diffusion controlled process, crystals of stoichiometric and off-stoichiometric composition can be grown. The feedback loop, where the growth quality can be judged and the growth conditions fine-tuned, includes X-ray diffraction and photoelectron emission tests.

Photocathode Depositions Using Hot Wall Evaporation

In accordance with an aspect of the present teachings, thin films of K$_2$CsSb photocathode films with various compositions can be prepared by hot wall evaporation onto glass substrates under a high vacuum (e.g., $10^{-6}$ to $10^{-7}$ Torr) condition. The films are deposited from vapor phases of different compositions derived from melt-grown pre-synthesized sources. The resulting quantum efficiencies of the thin film photocathode is measured in-situ and real time during the film growth to optimize the HWE parameters towards maximum conversion efficiencies for a given composition of the source material.

Figure 2:
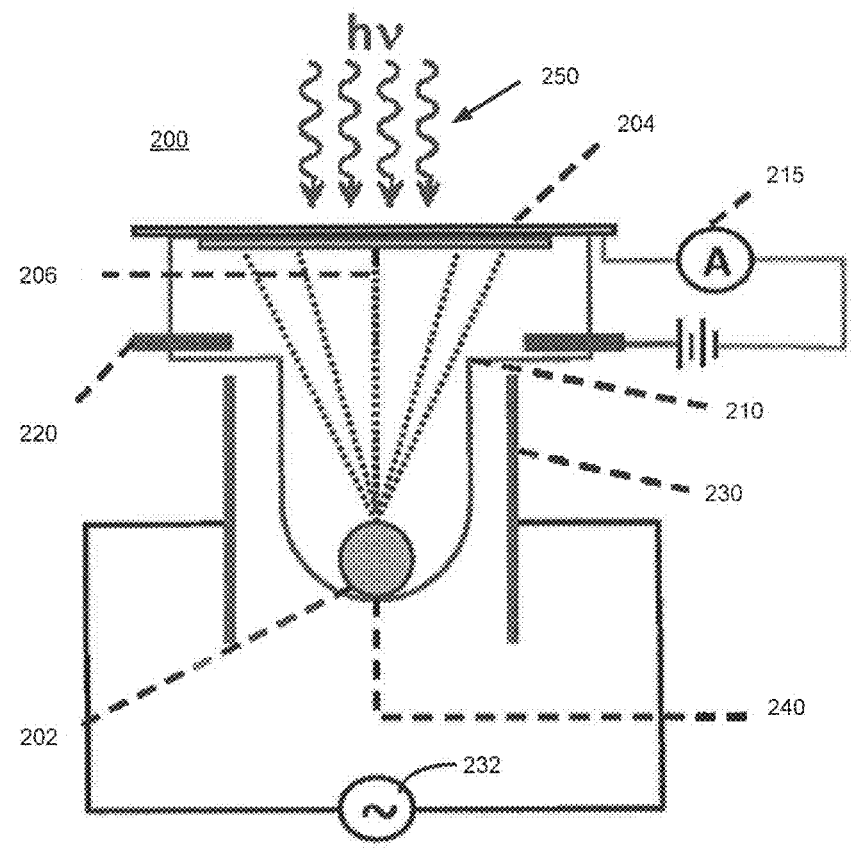
FIG. 2 schematically illustrates a deposition apparatus used for photocathode deposition and characterization, in accordance with one embodiment of the present teachings.

FIG. 2 schematically illustrates an apparatus used for photocathode deposition and characterization, in accordance with one embodiment of the present teachings. As shown in FIG. 2, a modified HWE apparatus 200 for thin film deposition (e.g., K$_2$CsSb) comprises, a glass crucible 210, a anode 220 coupled with glass crucible 210, a heater assembly 230 wrapping around glass crucible 220, a photocurrent measurement circuit 215 coupled between anode 210 and a glass substrate 204, and a thermocouple (or temperature feedback) 240 coupled to glass crucible 220. Heater assembly 230 is coupled to a transformer power supply 232.

Anode 210 is adapted to glass crucible 220 via a bonding alloy (such as a nickel-cobalt ferrous alloy, also known as Kovar®) suitable for high temperatures. The positioning of the anodic ring 210 is optimized to stay out of line-of-sight or remote from the source material during deposition, but has considerable visibility or proximate to deposited photocathode film 206 during in-situ photocurrent measurement. Glass substrate 204 may be pre-coated with thin metallic layers or with transparent conducting oxides to allow sizable photocurrent and a uniform electric field distribution over full cathode surface. The entire setup may be baked at a temperature of about 450° C. for about 48 hours in high vacuum to drive out moisture and other hydrocarbon contaminants.

Melt-down, pre-synthesized K$_2$CsSb source material 202 is loaded in the bottommost part of glass crucible 220 and vaporized congruently via heater 230. A thin film of photocathode 206 is deposited on the underside of glass substrate 204 in the line of sight. Electric bias is applied through an external circuit 215 between anode 220 and photocathode 206 to measure the photocurrent as a function of the wavelength of light 250 incident at the top surface of substrate 204. Thermocouple 240 located at the bottom of the HWE apparatus 200 provides the crucial feedback required to optimize the vaporization rate of K$_2$CsSb that optimizes the photocurrent generated for a desired wavelength of light. Output of the thermocouple 240 is provided to a control component in the heater 230 in order to provide feedback. In other embodiments, HWE of different compositions may be performed to arrive at a maximum QE. It should be noted that the method of these teachings differs from the conventional yo-yo method in that the deposition in the method of these teachings starts from the pre-synthesized K$_2$CsSb source material 202 wherein the conventional yo-yo method where Cs and K vapors are introduced sequentially, or K$_2$Cs vapor is introduced onto a heated Sb-coated glass substrates.

Photocathode Depositions Using E-Beam

In accordance with an aspect of the present teachings, an electron beam (e-beam) evaporation technique is deployed to address the challenge of different partial vapor pressure of the component chemicals (K, Cs, and Sb). This e-beam method utilizes high energy electron beam scanning and rapidly melting the pre-synthesized ternary compound K$_2$CsSb charge. The fast, explosion-like evaporation of the photocathode material has no time for preferential melting due to different partial vapor pressure-temperature functions of the alkali components and the antimony ($10^{-2}$ mbar vapor pressure reached at temperatures 667° C., 202° C., and 146° C. for Sb, K, and Cs, respectively, in the elemental form).

Figure 3:
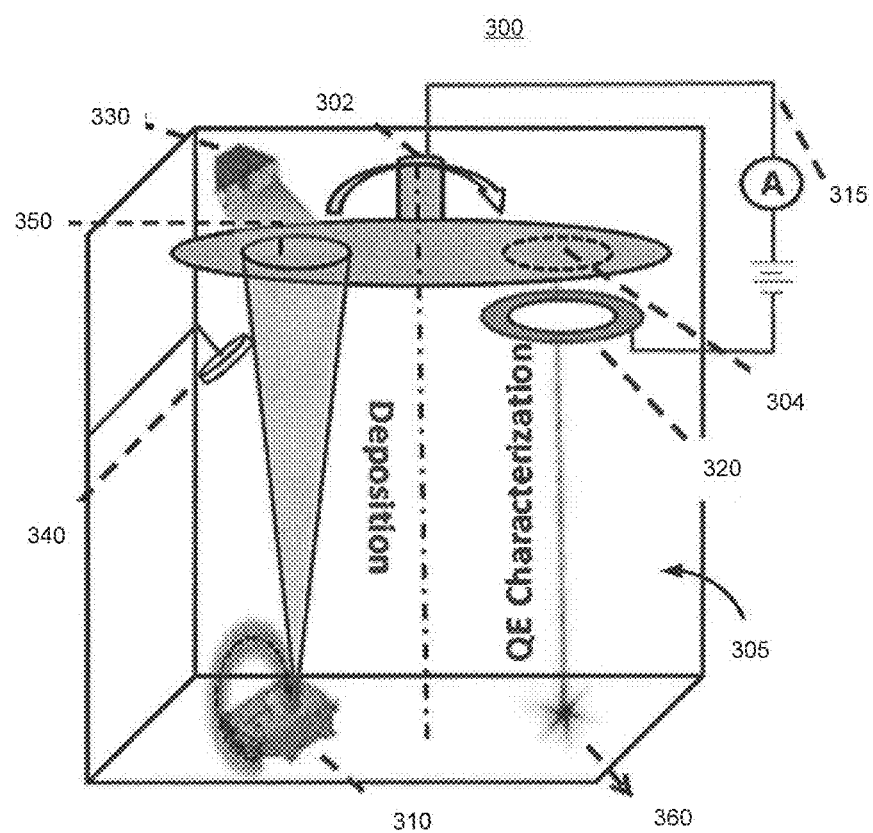
FIG. 3 schematically illustrates an e-beam apparatus including a vacuum chamber for synthesis and characterization of photocathode thin films, in accordance with an embodiment of the present teachings.

FIG. 3 schematically illustrates a deposition apparatus 300 including a vacuum chamber 305 for synthesis and characterization of thin film K$_2$CsSb, in accordance with an embodiment of the present teachings. As shown in FIG. 3, deposition apparatus 300 is largely divided into a deposition portion and a QE characterization portion. In one embodiment, apparatus 300 comprises, within vacuum chamber 305, a rotating substrate holder carousel 302 for holding a glass substrate 304, an e-beam gun 310 with pre-synthesized K$_2$CsSb source material, an anode 320 electrically coupled with carousel 302 through a circuit 315 for photocurrent measurement, a substrate heating lamp 330 for heating substrate 304, a thickness monitor 340 for monitoring the thickness of thin films formed on substrate 304, and substrate temperature feedback 350 for measuring the temperature of substrate 304. Rotating substrate holder carousel 302 comprises metallic bond to the photocathode formed on a substrate 304. The growth rates of photocathode may be controlled using a quartz thickness monitor.

The e-beam apparatus 300 provides the in-situ characterization of the grown photocathode in terms of quantum efficiency measurement. As shown in FIG. 3, the QE characterization is carried out in the right hand portion of the e-beam chamber 305, where a variable wavelength light source 360 is shining through a biased anode 320. In one embodiment, anode 320 is a metallic ring or a transparent conductive window, such as indium tin oxide or doped ZnO.

The bias electric field between anode 320 and carousel 302 can be as high as 30 kV/m and applied externally via electrical feed-through circuit 315 in chamber 305. The photocathode film formed on substrate 304 is simply rotated over to the characterization setup, such that it is in the line of sight of the light source 360 through transparent anode 320. The photocurrent can be read and used to calculate the quantum efficiency with respect to the corresponding excitation wavelengths. In other embodiments, many compositions can be tested to ensure the optimal performance of stoichiometry.

Photocathode

The performance of any photocathode is limited by the efficiency with which the photocathode emits electrons in response to incoming photons. The photocathode is generally a planar crystal. Each incident photon creates a hole-electron pair in the crystal, by elevating an electron from the valence band to the conduction band, leaving a hole in the valence band. In some instances, a material having a band-gap energy corresponding to the spectral region does not readily emit electrons from its surface when struck by photons, due to an energy barrier that arises at the crystal surface of the semiconductor. In order for surface emission to occur, the electron must overcome both the work function of the surface and the band gap energy of the semiconductor. Conventionally, this problem is overcome by "activating" the surface of the photocathode in such a manner that this energy barrier is overcome.

In one embodiment, a surface dipole similar is produced by delta doping. Doping-induced bandstructure engineering allows tailoring the work function. In an extreme case even a Negative Electron Affinity (NEA) can be achieved.

In a simplified ionic model Alkali atoms act as electron donor and Antimony as an acceptor. Consequently, an alkali deficiency can result in a deficiency of electrons, e.g. a p-doping of the material. To achieve the doping effect the activation energy of the carrier has to be thermally excited. A comparison between functionality and processing recipes indicates that at least some defects can be activated and that these defects significantly influence the electron emission behavior of the cathode. The strong ionic bonding character and diffraction data Indicate that at least the majority of defects are not point defects.

Photocathode Depositions Using Sputtering

Figure 2A:
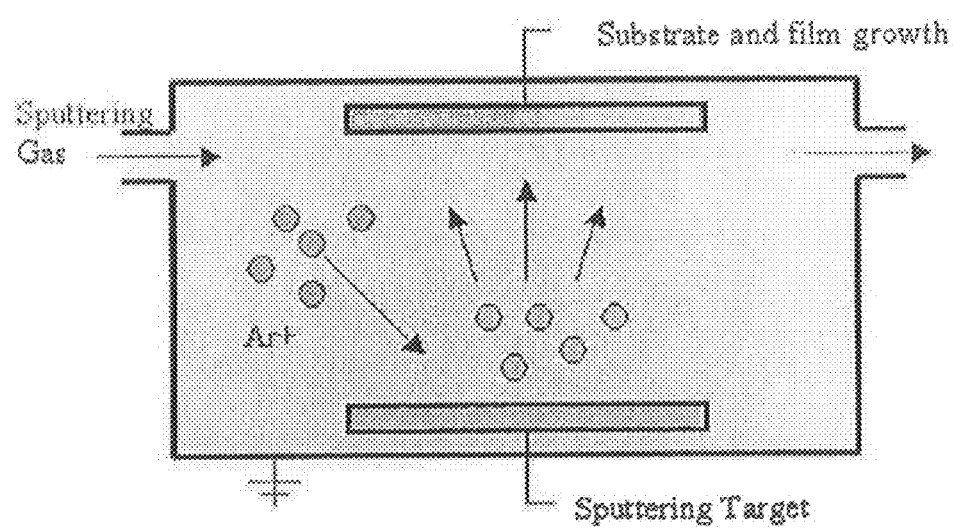
FIG. 2a schematically illustrates another deposition apparatus used for photocathode deposition and characterization, in accordance with another embodiment of the present teachings.

Sputtering is a process whereby atoms are ejected from a solid target material due to bombardment of the target by energetic particles (see FIG. 2A and Mattox, The foundations of Vacuum Coating Technologies, pp. 11-19, which is Incorporated by reference herein in its entirety and for all purposes). As disclosed herein below, the alkali deficiency can be obtained during sputtering. The alkali deficiency depends on the deposition conditions, whether sputtering or evaporation, and doping between $10^{-3}$ and $10^{-2}$ can be obtained.

In one embodiment, the sputter target is formed from the alkali antimonide powder in a glove box and under an inert atmosphere. The alkali antimonide powder is loaded onto a target holder and pressed and packed in order to make a film. A tin or Sb layer is deposited on top of the film. When the target is going to be used in sputtering, the tin or Sb layer is removed.

Band Structure Tailoring

One embodiment of the method of these teachings for band structure tailoring while sputtering is disclosed herein below for the exemplary embodiment of $K_2CsSb$. It should be noted that these teachings are not limited to the exemplary embodiment.

a.) Co-Evaporation of Cs and/or K During Film Sputter

Figure 4:
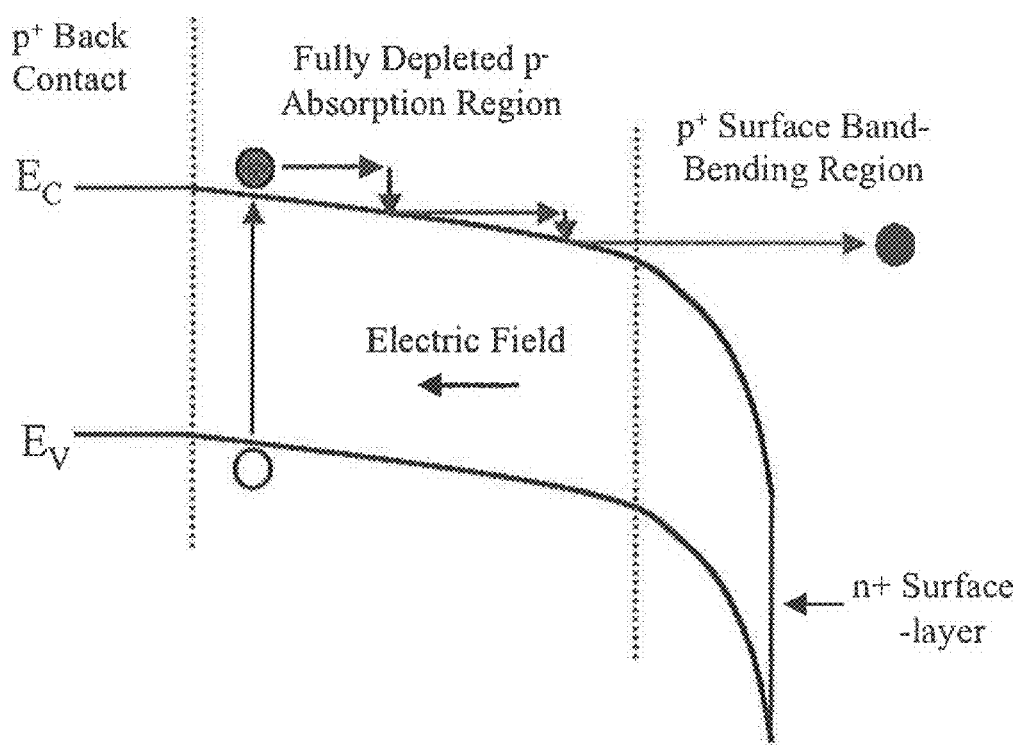
FIG. 4 shows an exemplary graphical representation of band bending induced by doping.

By changing the alkali concentration along the vertical direction of the cathode one can produce a gradient of the doping (for one exemplary configuration, see FIG. 4). Starting with a strong deficiency at the window interlayer one will create a strong p-doping noted as $p^{++}$. Gradually, the alkali concentration will be increased by additional alkali co-evaporation or co-sputtering of metallic alkali material. The co-evaporated material may be K, Cs, or K2Cs. Most likely, the material choice will influence the defect structure; Cs may be the first choice since it typically stabilizes the crystal structure. This stabilization may also promote a freezing of the concentration along the z-axis.

b.) Activation of the Alkali by Sputter Ion by Collision (Geometry of Coating Chamber is Chosen so that the Evaporated Alkali Vapor has to Penetrate Through the Plasma)

The reactivity and sticking coefficient of atoms depends on the charge state of the particle landing on the surface. By collisions with electrons or sputter gas inside the sputter plasma the charged state of the alkali ions can be tuned for increased reactivity. The enhanced reactivity (most likely the ionic state) will show a high sticking coefficient and a reduced mobility on the surface and into the film. Therefore a doping profile can be achieved by avoiding inter-diffusion.

c.) Use of Bias on Substrate to Preselect Activated Alkali Implementation

By applying a bias voltage predominantly ionized ions can be implanted into the surface. A comparison with other materials show that the resulted materials have most likely a higher density. There is also a high probability of creating a very chemically active surface avoiding large mobility.

d.) Use of a Low Temperature Substrate (RT) During Sputter to Prevent Migration Conserving Doping Profile; the Substrate Temperature is Kept at a Range Between about 5 C to about 20 C; Q By increasing the chemical reactivity one can reduce the annealing temperature to achieve a similar ordered state. This will allow conserving a vertical doping profile within the thin film.

e.) Short Term Heating (in the Order of 6 Hours) to a Predetermined Temperature, in One Instance 140 C-160 C, to Allow Annealing.

The last step of the film growth shall be an annealing step which will remove excessive non-reacted Cs and K, and removes dangling bonds at the grain boundaries. Both processes are linked since the alkali transport through the film requires a network of defects as they are found on the grain boundaries. During the transport Cs atoms will have a high probability to get absorbed on dangling bonds of Sb. Excessive Cs inside the grain boundary can diffuse to the surface. This process will require turning the temperature to a degree which allows mobilization of the excess and free Cs but does not affect the Cs already bonded to Sb.

Crystallographic Surface Orientation Selection

Figure 5A:
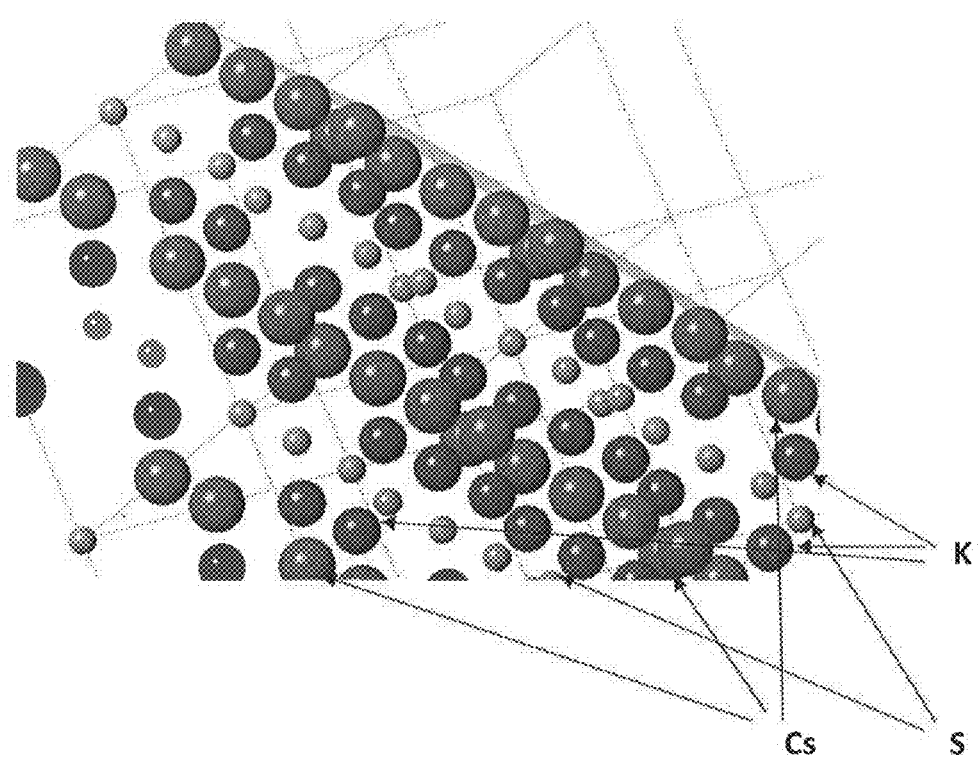
FIGS. 5a-5c show a representation of crystallographic orientations.
Figure 5B:
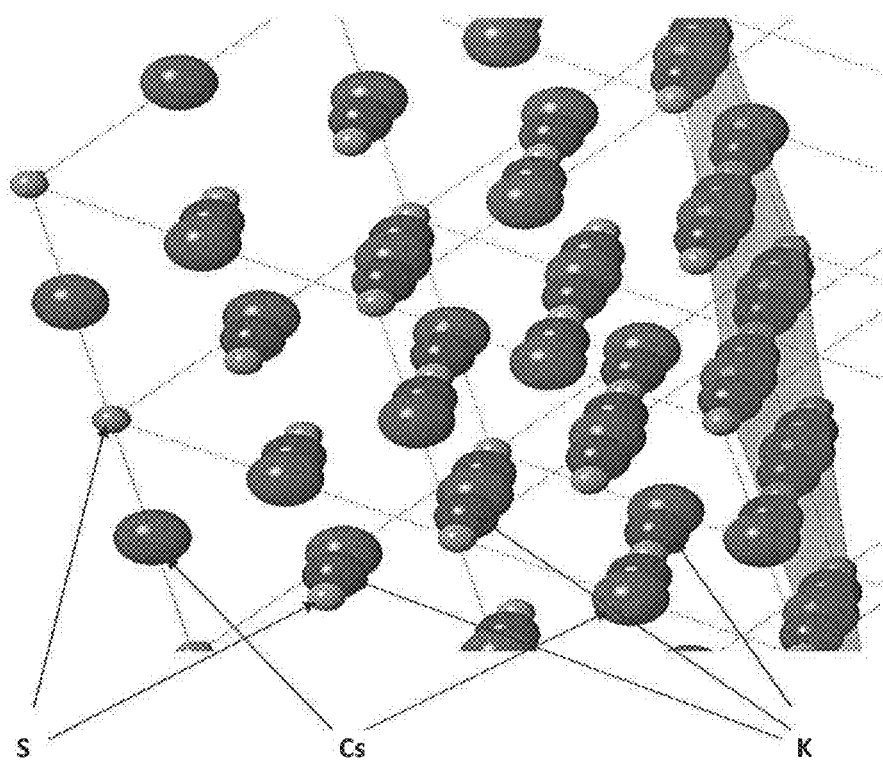
Figure 5C:
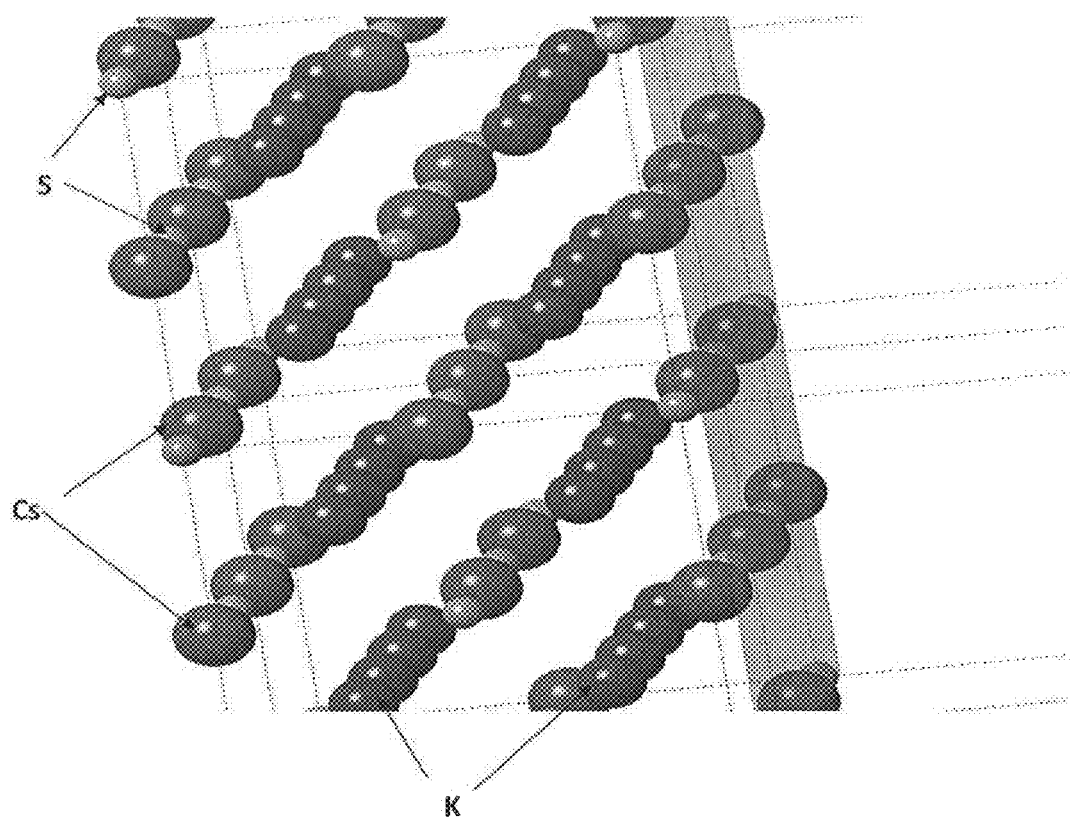

In a number of situations of interest, such as Delta doping, the change from p to n within a few monolayers, the surface texture or the crystallographic orientation of the surface has a significant impact. Each crystallographic surface orientation will have different prescriptions which result in a desired surface composition. Unfortunately, the stability of the different structures depends on the surface orientation so it is likely that prescriptions cannot be found for all surface orientations that can be used in a particular thin film component, such as, for example in a cathode. Orientation 111 and 110 appear to be preferable for cathodes. The highly isotropic band structure of the material makes it very unlikely that this is caused by a band structure property. Most likely it is caused by different surface energies or doping effects on the window interface. (The interpretation of the claims is not constrained by this explanation.) For a 111 orientation, a configuration can be obtained in which a Sb starting layer can be grown resulting in a p++ interface layer. FIGS. 5a-5c provide an illustration of 111 (5a), 110 (5b), and 100 (5c) orientation of crystallites. The atoms are represented by: Sb: brown (S), K: blue (K), Cs: purple (C).

In one embodiment, the method of the these teachings for obtaining a desired crystallographic surface orientation includes cesating substrate (multiple monolayers) with subsequent evaporation of mono layer Sb; subsequent heating of substrate to a predetermined temperature for the predetermined time, in one instance, about 400 C for about 30 min.

For the position on a glass surface, the strong chemical bond of Cs will reduce the glass surface; in combination with the high vapor pressure of Cs2O and CsO compounds a Si—Cs terminated surface will be followed by a Sb layer. The high temperature will ensure that all excessive Cs, and all Cs—O compounds are evaporated. Note that the first layer will show a Si—Sb bond followed by a Cs layer. Therefore this recipe should produce a 111-termination when a pre-synthesized antimonide material, comprising one or more alkali materials and antimony, where one of the alkalis is Cs, is deposited on the substrate after preparation.

Creating Delta Doping on Window-Thin Film Component and Thin Film Component-Vacuum Interface The positive electron affinity of the multialkali antimony thin film component, a cathode in one exemplary embodiment, can be changed to negative electron affinity by creating a P-N junction in the surface layer. This will not only increase the thermal noise of the device since thermally excited carriers can be easily emitted but will also allow increasing the red response of the cathode. A second effect will be that the cathode thickness can be increased since energetic losses of the carriers due to scattering can be tolerated.

It is important to notice that the annealing process as described above will significantly reduce the free thermally excited carriers. The number of free carriers depends on the band structure and a material constant in the case that doping levels play a small role. In the instance where the substrate is glass, Si with a similar band gap has about $10^{10}/cm^3$ electrons thermally excited at RT, a significantly increased recombination rate for excited carriers can be expected due to the flat band structure of the multialkalis (Si is has an indirect band gap) so that the carrier density should be significantly decreased at least by 2-orders of magnitude. With a carrier density of Si one would expect a "dark count rate" of about $10^4$ electrons/s/cm$^2$.

The embodiment of the method of these teachings disclosed herein below provides a prescription that will result in a delta-doping (change from p to n within a few mono layers). The embodiment of the method of these teachings disclosed herein below requires a surface texture or the crystallographic orientation of the surface, obtained as disclosed herein above.

The thin film component of these teachings is sputtered onto the substrate and the band structure tailoring method disclosed hereinabove is performed up to step (d).

(a) After performing step (d) in the band structure tailoring method disclosed hereinabove, a delta layer with n-doping is formed.

A surface such as shown in FIG. 5a or 5b with a number of Cs and K defects resulting from the stoichiometric condition is formed. By stopping the sputter process and providing Cs evaporation at low substrate temperatures one will create a solid Cs top-layer filling all defects with Cs. The substrate temperature is kept at the range disclosed herein above.

(b) final curing of the film using fast heating to prevent interdiffusion (in one instance, IR heating for short time) and pumping for multiple hours before sealing detector. Rapid thermal annealing is provided during final curing; in one instance, the curing time is between about 10 to about 15 seconds.

This process will remove excessive Cs so that only chemisorbed Cs is on the surface. The flash desorption will also provide enough energy to the Cs to anneal any surface defects by providing enough mobility to the surface Cs atoms without introduce large energy into the layer allowing inter-diffusion.

Although the above description uses a photocathode as an exemplary embodiment of the thin film component, it should be noted that other embodiments of the thin film component are also within the scope of these teachings. The above disclosed method can be used for band structure tailoring of other alkali antimonide thin film components.

Photocathode Characterizations

A component of the present teachings is the capability to measure the QE of the photocathode and correlate the structure results with the QE of the photocathode. Depending on the needs, either a single wavelength light source or a wide band light source may be used to probe the sample with a high resolution monochromator, allowing measuring the full spectral response. The photo response of the photocathode is measured by the total yield sample current, directly measuring the required current to bring the cathode to ground-potential.

The full spectral response provides first insights into the functionality of the photocathode. The photoelectrons are predominantly produced at different depths in the photocathode. Blue photons are mainly absorbed at the window entrance side and have originally a high kinetic energy whereas red photons are produced throughout the full cathode and have a low kinetic energy. Consequently, the efficiency in the red part of the spectrum is strongly dependent on the work function, e.g., the surface composition, whereas the blue sensitivity is mainly determined by the scattering path of the photoelectron before reaching the surface. These properties may be inferred based on the measurements.

Experimentally, it is relatively easy to measure 1 pA sample current. Over the course of a cathode production, one needs to measure QE of about 0.001% up to 50%. To see the full dynamics, one needs about 100 points for a spectrum, which should be measured within 1 sec. This relates to a required photon flux of $10^{14}$ photons/second or about 10 J power within sub-meV band pass. This can be easily provided by lasers or light emitting diodes.

In addition to the QE measurements, some of the following techniques are routinely used for photocathode characterization, such as (i) in-situ X-ray diffraction (XRD) and X-ray reflectivity tool, (ii) X-ray reflectivity (XRR), and (iii) in-situ X-ray photoelectron spectroscopy (XPS) and atomic force microscope (AFM).

In-situ X-ray diffraction (XRD) and X-ray reflectivity tool. XRD is a well known characterization technique which brings quantitative insight in the chemical composition of polycrystalline multiphase compounds. Applied to thin films, it also reveals the orientation of the individual crystallite, e.g., the texturing of the film. The combination of area detectors and high brightness synchrotron sources permits to take snap-shots of the structure within seconds making a movie like data-acquisition possible.

X-ray Reflectivity (XRR). Another important information is the mesoscopic structure of the film, e.g., the thickness and roughness of the film. This can be determined by measuring the specular and off-specular reflection of the primary beam from the sample, namely, X-ray Reflectivity (XRR).

In-situ X-ray Photoelectron Spectroscopy (XPS) and Atomic Force Microscope (AFM). The XRD and XRR measurement are complemented with a set of experiments, providing important information on the surface chemistry, non-crystalline compounds, contaminations, and the microscopic view of the surface.

For the purposes of describing and defining the present teachings, it is noted that the term "substantially" is utilized herein to represent the inherent degree of uncertainty that may be attributed to any quantitative comparison, value, measurement, or other representation. The term "substantially" Is also utilized herein to represent the degree by which a quantitative representation may vary from a stated reference without resulting in a change in the basic function of the subject matter at issue.

Although embodiments of the present teachings have been described in detail, it is to be understood that such embodiments are described for exemplary and illustrative purposes only. Various changes and/or modifications may be made by those skilled in the relevant art without departing from the spirit and scope of the present disclosure as defined in the appended claims.

What is claimed is:

1. A method for synthesizing an alkali semi-metal compound, wherein a semi-metal is a semi-metal in Group 15, the method comprising:
    mixing, at a temperature from about 15° C. to about 30° C. and at an ambient pressure from about 750 torr to about 800 torr, least two alkali materials to form an alloy composition; and
    mixing, at a temperature from about 15° C. to about 30° C. and at an ambient pressure from about 750 torr to about 800 torr, a solid semi-metal material and the alloy composition to form the alkali semi-metal compound;
    wherein the at least two alkali materials comprise a first alkali material and a second alkali material; and wherein the alkali semi-metal compound is a crystal compound.

2. The method of claim 1 wherein the alloy composition is a liquid alloy composition.

3. The method of claim 1 wherein the semi-metal material is antimony.

4. The method of claim 3, wherein the first alkali material comprises potassium (K), the second alkali material comprises cesium (Cs), the liquid alloy composition comprises $K_2Cs$, and the ternary crystal compound comprises $K_2CsSb$.

5. The method of claim 1, wherein the method is performed in an enclosed environment.

6. The method of claim 5, wherein the enclosed environment is a non-oxidizing environment containing inert gas, and wherein the enclosed environment is purified to contain less than about 0.5 ppm of oxygen ($O_2$) and water ($H_2O$).

7. The method of claim 6 wherein the inert gas is nitrogen or argon.

8. The method of claim 1, further comprising, upon mixing the solid semi-metal material and the liquid alloy composition, spontaneously forming the crystal compound without external physical interference.

9. The method of claim 1, wherein the alkali semi-metal compound comprises a nano-crystalline grain structure.

10. A method for fabricating a thin film component, comprising:
    providing pre-synthesized semi-metal compound material, the semi-metal compound material comprising one or more alkali materials and a semi-metal material;
    wherein the alkali semi-metal compound is a crystal compound;
    wherein pre-synthesizing the semi-metal compound material comprises:
        mixing, at a temperature from about 15° C. to about 30° C. and at an ambient pressure from about 750 torr to about 800 torr, at least two alkali materials to form an alloy composition; and
        mixing, at a temperature from about 15° C. to about 30° C. and at an ambient pressure from about 750 torr to about 800 torr, a solid semi-metal material and the alloy composition to form the alkali semi-metal compound; and
    A) depositing a thin film of the semi-metal compound material on a substrate to form the thin film component.

11. The method of claim 10 wherein the semi-metal material is antimony.

12. The method of claim 10 wherein the thin film component is a photocathode.

13. The method of claim 12 further comprising:
    B) measuring a quantum efficiency of the cathode; and
    C) repeating A) and B) until the quantum efficiency is greater than a predetermined value.

14. The method of claim 13, wherein B) comprises:
    B1) applying an electric bias between an anode and the cathode;
    B2) illuminating a light of a wavelength to the cathode; and
    B3) measuring a photocurrent between the anode and the cathode as a function of the wavelength to obtain the quantum efficiency.

15. The method of claim 14, wherein the anode comprises a metallic ring configured to stay remote from a location of the semi-metal compound material and proximate the cathode.

16. The method of claim 10, wherein the at least two alkali materials are a first alkali material and a second alkali material.

17. The method of claim 16, wherein the first alkali material comprises potassium (K), and the second alkali material comprises cesium (Cs).

18. The method of claim 17 wherein the semi-metal material is antimony, and wherein the semi-metal compound material comprises $K_2CsSb$.

19. The method of claim 16, wherein the first alkali material comprises potassium (K), the second alkali material comprises cesium (Cs), and the liquid alloy composition comprises $K_2Cs$.

20. The method of claim 10, wherein A) comprises:
   A1) depositing the thin film of the semi-metal compound material using one of a hot wall evaporation apparatus, sputtering and an e-beam deposition apparatus.

21. The method of claim 10 wherein the alloy composition is a liquid alloy composition.

22. The method of claim 10 further comprising co-evaporating, during deposition, at least one alkali material from the at least two alkali materials in order to alter alkali concentration along a direction perpendicular to the substrate.

23. The method of claim 10 further comprising, before deposition, preparing the substrate in order to obtain a predetermined crystallographic surface orientation.

24. The method of claim 10 wherein the thin film component is a photovoltaic component.

25. A method fabricating a thin film component, the method comprising:
   providing pre-synthesized semi-metal compound material, the semi-metal compound material comprising one or more alkali materials and a semi-metal material; and
   depositing a thin film of the semi-metal compound material on a substrate to form the thin film component;
   co-evaporating, during deposition, at least one alkali material from the one or more alkali materials in order to alter alkali concentration along a direction perpendicular to the substrate;
   activating a portion of the at least one alkali material by collisions in a sputter plasma;
   applying a bias voltage on the substrate in order to preselect activated alkali implementation;
   keeping the substrate at a predetermined temperature during deposition in order to prevent migration and to preserve a doping profile; and
   annealing the thin film component by heating at a predetermined temperature for a predetermined time.

26. The method of claim 25 wherein the at least one alkali material is cesium (Cs).

27. A method for fabricating a thin film component, comprising:
   providing pre-synthesized semi-metal compound material, the semi-metal compound material comprising one or more alkali materials and a semi-metal material;
   before deposition, preparing a substrate in order to obtain a predetermined crystallographic surface orientation; and
   depositing a thin film of the semi-metal compound material on the substrate to form the thin film component;
   wherein preparing the substrate comprises:
   depositing a number of monolayers of cesium on the substrate;
   depositing a monolayer of the semi-metal material on an outer monolayer from the number of monolayers of cesium; and
   heating the substrate to a predetermined temperature for a predetermined time.

28. The method of claim 27 further comprising:
   co-evaporating, during deposition, at least one alkali material from the one or more alkali materials in order to alter alkali concentration along a direction perpendicular to the substrate;
   activating a portion of the at least one alkali material by collisions in a sputter plasma;
   applying a bias voltage on the substrate in order to preselect activated alkali implementation;
   keeping the substrate at a predetermined temperature during deposition in order to prevent migration and to preserve a doping profile;
   forming a Delta layer with n-doping on an outer surface of the thin film component; and
   curing the thin film component by heating for a second predetermined time configured to prevent interdiffusion and pumping for a third predetermined time.

29. The method of claim 28 wherein forming the Delta layer with n-doping comprises stopping deposition and evaporating the at least one alkali while the substrate is at a second predetermined temperature.

30. The method of claim 29 wherein deposition was by sputtering and wherein the at least one alkali is cesium (Cs).

31. A method for fabricating a target for depositing an alkali semi-metal compound, the method comprising:
   loading the alkali semi-metal compound onto a target holder, wherein a semi-metal is a semi-metal in Group 15, synthesized by the method of:
      mixing at least two alkali materials to form an alloy composition; and
      mixing a solid semi-metal material and the alloy composition to form the alkali semi-metal compound;
      wherein the alloy composition is a liquid alloy composition;
      wherein the one or more alkali materials comprise a first alkali material and a second alkali material; and
      wherein the alkali semi-metal compound is a crystal compound;
   forming a film from the alkali semi-metal compound by pressing and packing; and
   depositing a layer of a passivating material on a top surface of the film.

32. The method of claim 31 wherein the semi-metal material is antimony.

33. The method of claim 32 wherein the passivating material is antimony.

34. The method of claim 31 wherein the method is practiced in a glove box.

35. The method of claim 31 further comprising:
   removing the layer of passivating material before deposition.

* * * * *